(12) United States Patent
Abel et al.

(10) Patent No.: US 11,703,447 B2
(45) Date of Patent: Jul. 18, 2023

(54) MEASUREMENT APPARATUS FOR MEASURING THE CONCENTRATION OF A GASEOUS SUBSTANCE

(71) Applicant: EPPENDORF SE, Hamburg (DE)

(72) Inventors: Philipp Abel, Hamburg (DE); Andreas Graff, Hamburg (DE)

(73) Assignee: Eppendorf SE, Hamburg (DE)

( * ) Notice: Subject to any disclaimer, the term of this patent is extended or adjusted under 35 U.S.C. 154(b) by 977 days.

(21) Appl. No.: 16/467,935

(22) PCT Filed: Dec. 8, 2017

(86) PCT No.: PCT/EP2017/082075
§ 371 (c)(1),
(2) Date: Jun. 7, 2019

(87) PCT Pub. No.: WO2018/104529
PCT Pub. Date: Jun. 14, 2018

(65) Prior Publication Data
US 2019/0339196 A1    Nov. 7, 2019

(30) Foreign Application Priority Data
Dec. 9, 2016    (EP) .................................... 16203297

(51) Int. Cl.
*G01N 21/35* (2014.01)
*G01N 21/3504* (2014.01)
(Continued)

(52) U.S. Cl.
CPC ......... *G01N 21/3504* (2013.01); *C12M 41/34* (2013.01); *G01N 33/004* (2013.01);
(Continued)

(58) Field of Classification Search
CPC ............ G01N 21/3504; G01N 33/004; G01N 2021/3125; G01N 2201/0231;
(Continued)

(56) References Cited

U.S. PATENT DOCUMENTS 5,059,397 A * 10/1991 Melly ................ G01N 21/3504
356/438
5,792,427 A * 8/1998 Hugh ...................... E06B 7/231
55/467
(Continued)

FOREIGN PATENT DOCUMENTS

| CN | 203941102 U | 11/2014 | |
| DE | 10220668 A1 * | 11/2003 | ......... G01N 21/3504 |

(Continued)

OTHER PUBLICATIONS

Distler, Paul "Use of Hot Air Sterilization to Protect CO2 Incubators From Contamination", American Laboratory, vol. 36, No. 4 (2014).

*Primary Examiner* — Marcus H Taningco
(74) *Attorney, Agent, or Firm* — Todd Lorenz

(57) ABSTRACT

The invention relates to a measurement apparatus for measuring the concentration of a gaseous substance. The apparatus comprises a light source, a light sensor, and a housing comprising at least one first housing member having a low thermal conductivity. A light path is formed from said light source to said light sensor, wherein the light path passes through a measurement region within said housing. The light source is configured to emit light with a spectral distribution such that said light is absorbed by said gaseous substance. Said light sensor is configured to receive the light emitted by the light source after it has passed through the measurement region. The first housing member comprises a thermal shielding region facing said measurement region on its one (Continued)

Figure 1:
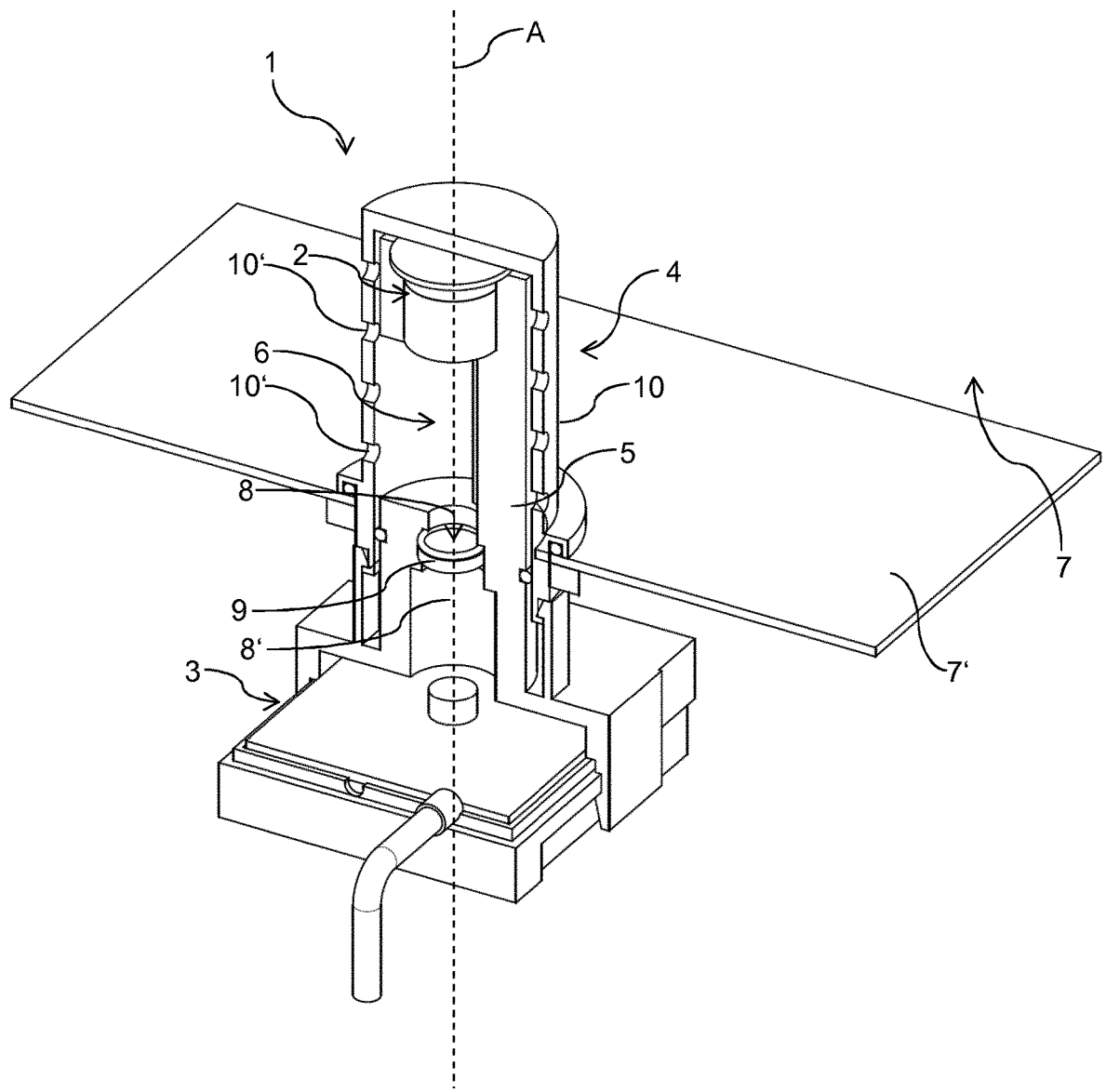

side and said light sensor on its other side, and is configured to permit the passage of light.

15 Claims, 2 Drawing Sheets

(51) Int. Cl.
*C12M 1/34* (2006.01)
*G01N 33/00* (2006.01)
*G01N 21/31* (2006.01)

(52) U.S. Cl.
CPC ............. *G01N 2021/3125* (2013.01); *G01N 2201/0231* (2013.01); *G01N 2201/0238* (2013.01)

(58) Field of Classification Search
CPC ..... G01N 2201/0238; G01N 2201/023; C12M 41/34; C12M 41/14
See application file for complete search history.

(56) References Cited

U.S. PATENT DOCUMENTS

| | | | |
|---|---|---|---|
| 5,886,348 A * | 3/1999 | Lessure | G01N 21/3504 250/339.04 |
| 6,114,700 A * | 9/2000 | Blades | G01N 21/05 250/343 |
| 6,255,653 B1 * | 7/2001 | Kouznetsov | G01N 21/3504 250/338.5 |
| 2003/0111607 A1 * | 6/2003 | Bachur, Jr. | G01N 21/3504 250/343 |
| 2004/0211902 A1 * | 10/2004 | Stahl | G01N 21/3504 250/339.12 |
| 2006/0023299 A1 * | 2/2006 | Muraki | C12M 41/14 359/368 |
| 2009/0323068 A1 | 12/2009 | Yamakage et al. | |
| 2011/0304844 A1 | 12/2011 | Willing et al. | |

FOREIGN PATENT DOCUMENTS

| | | | | |
|---|---|---|---|---|
| DE | 10220668 A1 | 11/2003 | | |
| DE | 102010055182 | 6/2012 | | |
| DE | 202010017994 U1 | 7/2013 | | |
| JP | H04158244 A | 6/1992 | | |
| JP | 2000139453 A | 5/2000 | | |
| JP | 2006191831 | 7/2006 | | |
| JP | 2006201101 A1 | 8/2006 | | |
| WO | WO-9922221 A1 * | 5/1999 | | ......... G01N 21/3504 |
| WO | WO 2012084162 A1 | 6/2012 | | |

* cited by examiner

MEASUREMENT APPARATUS FOR MEASURING THE CONCENTRATION OF A GASEOUS SUBSTANCE

The present invention relates to the field of measurement apparatuses for measuring the concentration of a gaseous substance, to the field of incubators comprising such a measurement apparatus for measuring the concentration of a gaseous substance in a gaseous content contained in such incubators, and methods of manufacturing or operating such incubators. Specifically, the present invention is directed to disinfectable incubators.

Such incubators are typically used in biology or biotechnology to grow, cultivate, maintain, and process cell cultures or microbiological cultures. For this purpose, such incubators provide a chamber with a controlled environment filled with a gaseous content, typically air, into which the cell cultures or microbiological cultures can be placed. In particular, the temperature, the humidity, and/or the carbon dioxide concentration inside the chamber is controlled by such incubators.

Specifically, the carbon dioxide concentration is measured by a carbon dioxide measurement apparatus extending into the chamber and is controlled, particularly by adding carbon dioxide to the gaseous content in said chamber, to allow controlling the pH value of culture media of said cell cultures or microbiological cultures cultivated therein in cell culture vessels. Generally, a high humidity inside said chamber prevents drying out of culture media and a predetermined temperature provides, together with the high humidity, a suitable environment for growing cell cultures or microbiological cultures in cell culture vessels.

However, undesired or even detrimental cells, microorganisms, bacteria, fungi, algae and the like may also prosper in such an environment, especially on the walls of the chamber or in an water bath contained in the incubator chamber. Thus, it is necessary to keep such an incubator, in particular the chamber of such an incubator, clean and moreover to disinfect, preferably sterilize the interior, in particular the chamber of the incubator.

Generally, disinfection is performed regularly after a certain time span or upon an infection.

Typically, such incubators are disinfected by heating the interior. Since the measurement apparatuses, in particular said carbon dioxide measurement apparatus, are in contact with the interior, and in particular extend into said chamber, they are also exposed to the heat required for disinfection of the incubator. Thus, said measurement apparatuses have to be removed prior to starting such a disinfection procedure to avoid damaging them, or sophisticated and expensive measurement apparatuses have to be used that are able to operate at or at least can withstand the required temperatures.

A measurement system for measuring the carbon dioxide concentration in an incubator also at high temperatures is disclosed in DE 10 2010 055 182 A1 by Baschant et al. A radiation source and at least two, preferably three radiation detectors are arranged such that radiation emitted from the radiation source is receivable by said detectors after passing through a measurement volume and a channel having a smaller diameter than the measurement volume. Each detector is located at that end of its channel facing away from the light light source. The other end of the channel is facing said measurement volume. Said detectors are mounted and said channels are formed in a lid piece of the measurement system. In this manner, the incidence of scattered light onto said detectors is virtually eliminated. However, said lid piece is preferably made of aluminum, which has a high thermal conductivity and which therefore is not suitable to thermally shield the detectors without further cooling.

Temperature differences between the incubator and a measurement system or measurement apparatus may result in unwanted condensation. In order to prevent condensation, JP 3897336 B2 discloses a measurement apparatus with a protection cylinder having water repellency and breathing properties and enclosing an electric heating element as well as an infrared type carbon dioxide sensor.

US 2004/211902 A1 describes a measuring device for determining the concentration of gases by infrared absorption, comprising a radiation source which is arranged, together with a radiation detector disposed in the radiation path, inside a housing which is sealed in a gas-tight manner in relation to the gas which is to be measured. An infrared permeable window is arranged in the radiation path between the radiation source and the radiation detector. Said window seals the inside of the housing in relation to the gas which is to be measured. The document does not describe details of using the measurement device with the incubator or details on how the measuring device can be installed or mounted to an incubator. This also applies for the document DE 102 20 668 A1, which is related to a gas sensor comprising a measurement chamber, which is a separate unit consisting of closed walls besides entry and exit holes for the gas. It is an object of the present invention to provide a measurement apparatus for measuring the concentration of a gaseous substance in a chamber, which in particular facilitates a disinfecting procedure of said chamber and/or may improve an incubator equipped with such a measurement apparatus, particularly with regards to operability and reliability.

A solution to this problem is provided by the teaching of the independent claims, specifically by a measurement apparatus according to claim 1, and an incubator according to claim 12, a method of manufacture of an incubator according to claim 14, and a method of operating an incubator according to claim 15. Various preferred embodiments of the present invention are particularly provided by the teachings of the dependent claims.

A first aspect of the present invention is directed to a measurement apparatus for measuring the concentration of a light absorbing gaseous substance in a chamber. The measurement apparatus comprises a light source, a light sensor, and a housing comprising at least one first housing member having, preferably, a low thermal conductivity. Furthermore, a light path is formed from said light source to said light sensor, wherein the light path passes through a measurement region within said housing and wherein the housing is communicatively connectable to said chamber such that a gaseous content of said chamber may be exchanged with, and in particular flow to said measurement region. In addition, the light source is configured to emit light with a spectral distribution such that said light is absorbed at least partially and dependent on the concentration of said gaseous substance in said gaseous content. Moreover, the light sensor is at least partially arranged within said first housing member and outside said measurement region. Additionally, said light sensor is configured to receive the light emitted by the light source after it has passed through the measurement region. Moreover, the first housing member comprises a thermal shielding region facing or forming a part of said measurement region on its one side and facing said light sensor on its other side. The thermal shielding region is configured to permit the passage of light along said light path from its one side to its other side.

Preferably, the first housing member is an integrally formed part, i.e. it cannot be separated into individual parts like a base part or a holder without causing damage. Preferably, the first housing member is made from, or at least comprises, at least one plastic material, and/or preferably is formed by injection molding. This allows a low cost production and provides mechanical stability to the first housing member. The first housing member has a base part for connecting the light sensor and, preferably, has a holder part for holding the light source. The first housing member comprises a thermal shielding region, which is preferably arranged between the base part and the holder part. When placed accordingly for operation to measure the gaseous substance inside an incubator chamber, it is preferred that the holder part is positioned inside the chamber and/or it is preferred the base part is positioned outside the chamber. The first housing member may have an elongated shape, preferably a substantially cylindrical shape.

The term "chamber" in the sense of the present invention particularly refers to a device providing an inner space that is separated from the outside. Preferably, chamber refers to an enclosure that may contain a gaseous content. In particular, the chamber may comprise one or more boundary walls defining said inner space. Moreover, a chamber may comprise one or more closable openings, in particular access openings, apertures, holes, mounting holes and/or doors, particularly to enable accessing the inner space of the chamber. Preferably, at least when said openings are closed, the chamber limits or preferably, at least essentially, prevents the flow of its gaseous content to the outside and/or entry of substances from the outside to its inner space. Moreover and preferably, the chamber limits or preferably, at least essentially, prevents the exchange of heat between its inner space and the outside by insulating the inside from the outside, particularly by means of an insulating material which may be arranged near or attached to said boundary walls. Thus, a chamber in the sense of the present invention may provide and/or maintain an environment in its inner space with a gaseous content and/or temperature that is different from the outside.

An element having a "low thermal conductivity" in the sense of the present invention particularly refers to an element that limits a transfer of heat from one region of the element to another region of the element. The thermal conductivity of such an element typically depends on the material or materials out of which said element is made. In particular, materials such as plastics, e.g. polyurethane, acrylic glass, polystyrene, rubber, or Teflon, wood, and cork have a low thermal conductivity, whereas materials such as metals, e.g. iron, steel, titanium, aluminum, or copper, silicon carbide, and aluminum nitride have a high thermal conductivity. Moreover, the thermal conductivity may depend on the structure of said element or on the inner structure of material, e.g. thermal conductivity may differ along different crystal axes, or the presence and arrangement of multiple layers of different materials forming said element. In particular, the thermal conductivity may depend on the geometrical structure of said element, wherein e.g. smaller cross-sectional areas result in a lower thermal conductivity. Preferably, an element having a low thermal conductivity in the sense of the present invention may comprise several layers of different materials, wherein one or more of these materials have a low thermal conductivity. Alternatively and preferably, an element having a low thermal conductivity in the sense of the present invention may consist of one layer and/or may be made of a single material. Preferred materials are Teflon, Polyetherimide, Polysulfones, and/or Polyaryletherketones (PAEK) such as Polyether ether ketone (PEEK). Also preferably, an element having a low thermal conductivity in the sense of the present invention may comprise gas filled or vacuumized compartments, e.g. as in case of a heat insulation foam or a thermos flask.

In the sense of the present invention "light" refers to electromagnetic radiation in the infrared, visible light, and ultraviolet electromagnetic spectrum. Preferably, such electromagnetic radiation has a wave length of at least 100 nm, preferably at least 500 nm, preferably at least 1000 nm, preferably at least 3000 nm, and preferably at least 3950 nm as well as a wavelength of at most 1000 µm, preferably at most 100 µm, preferably at most 10 µm, and preferably at most 4260 nm. It is to be understood that light in the sense of the present invention may have a single wavelength or may be an electromagnetic radiation comprising multiple, different wavelengths, in particular a spectral distribution with one or more maximums, at which the energy density relating to the wavelength is the highest.

The term "light source" in the sense of the present invention particularly refers to an apparatus emitting electromagnetic radiation with wavelengths that are at least partially within the spectrum of light. In particular, a light source can emit light of a single wavelength, of multiple wavelengths, or with a spectral distribution of wavelengths. Moreover, a light source may be a heatable body radiating light according to the blackbody radiation and having a maximum of radiation that is dependent on its temperature.

The term "light sensor" in the sense of the present invention particularly refers to an apparatus that may receive light and generate one or more signals that depend on the intensity and/or spectral distribution of the received light. The light sensor may comprise a light sensitive surface, and may comprise a carrier element for carrying the light sensitive surface. The light sensitive surface may comprise thermocouples, as in the case of a thermopile, or a semiconductor. The carrier element may be a printed circuit board or a plate, preferably made from a plastic material.

By the term "configured" in the sense of the present invention it is particularly to be understood that the corresponding apparatus is already set, arranged or adjustable—that is, configurable—to perform a particular function. Preferably, the configuration may be performed via a corresponding setting of parameters of a process flow or of switches or the like for activating functions or settings. Also preferably, the configuration of the apparatus may be performed via an appropriate arrangement of parts of said apparatus.

Accordingly, the concentration of a light absorbing gaseous substance can be measured by its interaction with light. Furthermore, the measurement apparatus according to the present invention advantageously allows limiting the amount of heat passing to said light sensor, while permitting the passage of light to said light sensor. Thus, a light sensor may be employed that has a lower operating temperature and/or maximally tolerable temperature than the temperatures present in the chamber and/or measurement region, especially during a disinfecting procedure of said chamber. Therefore, the measurement apparatus may remain connected to said chamber, in particular of the incubator, while the temperature in said chamber exceeds the maximally tolerable temperature of the light sensor. A further advantage is that condensation, e.g. of water vapor present in the gaseous content of said chamber, may be at least essentially avoided or at least minimized, particularly by means of said first housing member which prevents a strong temperature gradient near its surface and/or reduces the amount of heat transferred from the measurement region to the outside and/or to said light sensor.

In the following, preferred embodiments of the measurement apparatus are described or can be gathered from the description, which can be arbitrarily combined with each other or with other aspects of the present invention, unless such combination is explicitly excluded or technically impossible.

According to a first preferred embodiment, said thermal shielding region has a tubular inner shape. This advantageously minimizes the inner surface of said thermal shielding region and/or allows the passage of light along its longitudinal axis.

In a preferred embodiment the inner shape of said thermal shielding region is elongated and long enough in relation to its width to provide a desired thermal shielding of said light sensor. Accordingly, an elongated shielding region separates the measurement region from the light sensor, allows the formation of a temperature gradient within said gaseous content along the longitudinal axis of the thermal shielding region, and/or limits the amount of heat transferred from said measurement region to said light sensor. Moreover, by choosing an appropriate relation of the length of said shielding region to the width of said shielding region a convection, in particular of the gaseous content of said chamber, may be essentially avoided or at least minimized, thus reducing the amount of heat transferred from said measurement region to said light sensor by said gaseous content.

For this purpose, according to a preferred variant the length of the inner shape of said thermal shielding region is at least 10 mm, preferably at least 20 mm, more preferred at least 28 mm and preferably less than 100 mm and/or the width of the inner shape of said thermal region is at most 70 mm, preferably at most 30 mm, and preferably at most 10 mm and preferably at least 2 mm. Moreover, these dimensions of said inner shape of said thermal region may advantageously permit total dimensions of the measurement apparatus that allow the mounting and/or manual handling of this variant to said chamber, in particular incubator. For example, the measurement apparatus may have a total length between 20 mm and 110 mm, preferably between 30 mm and 50 mm as well as a total width between 10 mm and 50 mm, preferably between 20 mm and 30 mm.

According to a preferred embodiment, an at least essentially gas tight window is arranged within said thermal shielding region and within said light path such that said window separates said measurement region from said light sensor. Furthermore, said window is configured to permit the passage of light to said light sensor, in particular light with a wavelength absorbed by the gaseous substance, e.g. in case of carbon dioxide, light with a wavelength of 4.26 µm or a spectral distribution with a maximum at 4.26 µm. Additionally, said window is configured to prevent the passage of gas from said chamber or measurement region to said light sensor in cooperation with the side of said thermal shielding region facing said light sensor. Accordingly, moisture, e.g. water vapor contained in said gaseous content, cannot enter the side of the thermal shielding region facing the light sensor, and condensation of moisture at or near said light sensor is avoided or at least minimized. Furthermore, by mounting said window within said thermal shielding region and on said first housing member said window at least essentially may be at a thermal equilibrium to said measurement region, thereby also avoiding or at least minimizing condensation at said window. In a preferred variant said window is made of sapphire glass, which provides a wide optical transmission band as well as a high permittivity of light, particularly in the infrared spectrum as especially beneficial for the measurement of a carbon dioxide concentration by absorption of specific wavelengths, e.g. 4.26 µm. In an alternate and preferred variant said window is made of a transparent plastic, which provides a lower thermal conductivity as compared to sapphire glass, thus further thermally isolating said light sensor from said measurement region and/or further reducing eventual condensation of moisture at said window.

According to a preferred embodiment, said light source is configured to emit light with at least two different wavelengths. Furthermore, the light of one of the at least two wavelengths is being absorbed by the gaseous substance, while the light of the other of at least two wavelengths is not absorbed. Moreover, said light sensor is configured to receive the at least two different wavelengths and to provide a signal characterizing the light intensity for each of the at least two different wavelengths. Thereby, a measurement signal and a reference signal are advantageously provided. Alternatively, the measurement apparatus may comprise said light sensor and an additional light sensor, each being sensitive to one of the at least two wavelengths. Thus, said light sensor may provide the measurement signal and the additional light sensor may provide the reference signal. It is to be understood, that the at least two different wavelengths may also refer to two different regions of a spectral distribution of light emitted by said light source. The reference signal and a measurement signal advantageously enable to compensate changes in the emitted light, at least as long as the light intensity of the two different wavelengths changes proportionally to each other. In a preferred variant the wavelength of the light for the reference signal is at least 3.8 µm and at most 4.1 µm and preferably 3.95 µm, and the wavelength of light for the measurement signal is at least 4.2 µm and most 4.3 µm and preferably 4.26 µm, which is particularly beneficial for measuring the carbon dioxide concentration.

According to a preferred embodiment, a reference light path is formed from said light source to said light sensor that does not pass through said measurement region. Alternatively, a reference light path is formed from said light source to said light sensor that at least partially passes through said measurement region, wherein the length of the section of said reference light path passing through said measurement region is either longer or shorter than the section of the light path passing through said measurement region. Accordingly, the absorption by said gaseous substance along said reference light path and along said light path differs proportionally to the different lengths passing through said measurement region. In particular, if said reference light path does not pass through the measurement region at all, light is not absorbed by said gaseous substance along this path. Thus, the received light intensities along the two different paths, reference light path and light path, may be used to compensate changes in the emission of said light source and/or sensitivity of said light sensor.

In a preferred embodiment, said light sensor comprises at least one first optical filter element that permits the passage of light with a wavelength that is absorbed by the gaseous substance and/or at least one second optical filter element that filters out light with a wavelength that is absorbed by the gaseous substance. This advantageously enables to permit the passage of light with a wavelength relevant for measuring the absorption to said light sensor, in particular to a first part of said light sensor, and/or to narrow the sensitivity of said light sensor, in particular to a second part of said light sensor, to wavelengths relevant for measuring a reference signal. Thus, especially the sensitivity of one or more sensor elements or parts of the sensor may be configured such that said sensor can provide a reference and a measurement signal. In particular, distortions caused by incident light of other wavelengths and/or changes in the light emitted by said light source and/or changes in the overall sensitivity of said light sensor can be reduced. In a first preferred variant, a reference path is provided from said light source to said light sensor that does not pass through the at least one first optical filter element. In an additional or alternate preferred variant, a reference path is provided from said light source to said light sensor that passes through the at least one second optical filter element. In an additional or alternate preferred variant, said light path passes through said measurement region and through the at least one first optical filter element. These variants may beneficially improve the reliability of the measurement of the concentration of said gaseous substance.

According to a preferred embodiment, said light sensor comprises a thermopile to convert the received and in particular filtered light into electrical energy serving as a signal characterizing the light intensity, in particular the light intensity of the light not being filtered out. This beneficially enables to convert the received light into electrical energy. Moreover, the thermopile is beneficial for a reliable measurement. Another benefit of a typical thermopile is its temperature resistance, in particular compared to typical semiconductor sensors.

According to a preferred embodiment, said light source comprises a heatable body to radiate said light. In a preferred variant, said heatable body is made of brass or ceramics and is, in particular, a brass rod or a ceramics rod. In a preferred variant, said light source comprises a heating device for heating said heatable body. In a preferred variant, said heatable body is heated to a temperature such that it emits infrared light. In particular, this allows a robust implementation of said light source. Furthermore, radiating infrared light is beneficial for measuring the carbon dioxide concentration. Moreover, said heatable body provides a broad emission spectrum. In particular, light of one wavelength of said broad emission spectrum may serve as light being absorbed by said gaseous substance, while light of another wavelength may serve as a reference, wherein changes of the heatable body or its temperature affect both wavelengths, at least as long as they are at least essentially close to each other, e.g. 3.95 µm and 4.26 µm.

According to a preferred embodiment, said first housing member is made of a material with low thermal conductivity, in particular plastics. This is particularly beneficial for a cost-effective production and/or for a reliable as well as durable thermal insulation by said first housing member.

According to a preferred embodiment, said housing further comprises at least a second housing member. This beneficially allows for use of different materials for said first and second housing member. Furthermore, said first and second housing member may be produced and/or formed separately, thus simplifying and rendering their production more cost-effective.

In a preferred embodiment, the at least one second housing member is made of a material with a higher thermal conductivity than the at least one first housing member. In a preferred variant, the at least one second housing member is made of metal. Providing the first housing member made from a material with a lower thermal conductivity is beneficial for providing thermal insulation. Providing the second housing member made from a mechanically stable material, in particular a metal, is beneficial for other functions such as mounting said measurement apparatus to said chamber by means of said second housing member.

According to a preferred embodiment, a gasket is arranged around said second housing member such that it seals a connection area between the measurement apparatus and said chamber, when the measurement apparatus is mounted to said chamber.

In a preferred embodiment, the at least one first housing member is at least partially arranged within said second housing member. In this manner, the housing can be mounted to said chamber by means of said second housing member, while the first housing member, which in particular carries the light sensor, is at least partially inserted into and/or mounted onto said second housing member. This beneficially facilitates production and/or mounting of said measurement apparatus.

In a preferred embodiment, the at least one first housing member and the at least one second housing member are each provided with one or more holes and/or recesses to permit the passage of gaseous content from said chamber to said measurement region and vice versa. In particular, the first or the second housing member can be provided with many holes and/or recesses, whereas the other is provided with only one hole or recess, which is larger than each of the many holes/recesses.

According to a preferred embodiment, said housing is configured to limit, and in particular to prevent the entry of light into said measurement region. In particular, said housing is configured to limit or prevent the entry of light in a direction along said light path or said reference light path. In a preferred variant, the at least one first and/or the at least one second housing member limits or prevents the entry of light by means of one or more holes, wherein the holes permit the passage of gaseous content on the one hand and on the other hand are arranged such that light passing through these holes is not directed to said light sensor. In particular, this makes the measurement more robust, especially when said chamber does not prevent or limit the entry of light into the chamber and/or the measurement region of said measurement apparatus.

A second aspect of the present invention is directed to an $CO_2$ incubator, in particular one for cell culture, comprising a chamber and at least one measurement apparatus for measuring the concentration of a light absorbing gaseous substance according to the first aspect of the invention. Furthermore, said chamber is configured to contain a gaseous content which may contain said gaseous substance, in particular to provide a controlled environment particularly for cell culture. Moreover, said at least one measurement apparatus, especially its measurement region, is communicatively connected to said chamber of the $CO_2$ incubator to permit the exchange of said gaseous content.

The term "incubator" in the sense of the present invention refers to an instrument by means of which controlled climatic conditions for various biological development and growth processes can be set up and maintained. For this purpose, the incubator provides a chamber with controlled climatic conditions. The incubator serves to set up and maintain a microclimate with regulated gas and/or humidity and special temperature conditions in an incubator space, particularly said chamber, wherein this treatment may be dependent on time. The incubator may preferably comprise a timer, a timer switch, a heater/cooling apparatus, and a setting for regulating a substitute gas supplied to the incubator space, in particular fresh air, a setting apparatus for the composition of the gaseous content in the incubator space of the laboratory incubator, in particular for setting the carbon dioxide and/or oxygen content of the gas and/or a setting apparatus for setting the humidity in the incubator space. Furthermore, the incubator preferably comprises a regulation apparatus with at least one control group, to which at least one heater/cooling apparatus is assigned as an actuator and at least one temperature measurement apparatus is assigned as a measurement member. Preferably, the temperature can be regulated in the incubator by means of the controlling system. Carbon dioxide incubators serve, in particular, for cultivating animal or human cells. Incubators may have turning devices for turning an at least one laboratory sample and/or a shaker apparatus for shaking or moving the at least one laboratory sample and/or one or more shelves for carrying the at least one laboratory sample. Moreover, the incubator may comprise a water bath, which is in particular temperature regulated, for supplying humidity to its gaseous content. This water bath is, in particular, arranged in the lower area of the incubator, in particular at the floor of said chamber. The instrument-controlled treatment of the at least one laboratory sample corresponds to a climate treatment in an incubator, with at least one sample being subjected to said treatment. Possible parameters, in particular program parameters, in particular user parameters, which are used to influence a climate treatment, define, in particular, the temperature of the incubator space, in which the at least one sample is incubated, the oxygen and/or carbon dioxide partial pressure incubator, the humidity in the incubator and/or at least one progress parameter, which influences or defines the progress, in particular the sequence, of an incubation treatment program consisting of a plurality of steps.

The embodiments and variants as well as potential benefits as already described in detail above in connection with the first aspect of the present invention also apply correspondingly to the incubator according to the present invention.

In the following, preferred embodiments of the incubator are described or can be gathered from the description, which can be arbitrarily combined with each other or with other aspects of the present invention, unless such combination is explicitly excluded or technically impossible.

In a first preferred embodiment, the incubator further comprises a front door, a rear wall, in particular opposite to the front door, and one or more gas inlets, wherein one of the gas inlets is configured to supply said gaseous substance into said chamber. Furthermore, the at least one measurement apparatus extends through a mounting hole in the rear wall. Moreover, said mounting hole and said gas inlets are positioned such that the minimum distance between said mounting hole and said gas inlets is at least one fourth of the diagonal length of said rear wall, preferably at least one third of it, more preferred at least half of it or at least half of the width of said rear wall, preferably two thirds of it, more preferred three quarters of it. In a preferred variant, said mounting hole is positioned in the upper right quadrant, in particular the upper right corner of the rear wall. In a preferred variant, said mounting hole is positioned such that it has a predetermined distance from the gas inlets, shelves, samples, and/or water baths of the incubator. This is beneficial to avoid or at least reduce distortions of the measurement by gas flowing into the incubator and/or by inhomogeneous distribution of the gaseous content near the gas inlets, shelves, samples, and/or water baths.

A third aspect of the present invention is directed to a method of manufacture of an incubator that is disinfectable by heating and configured to measure the concentration of a light absorbing gaseous substance in a gaseous content of said incubator. The method of manufacture comprises the following steps: In a first step, an incubator with at least one mounting hole is provided, wherein the incubator comprises a chamber to contain said gaseous content. In a second step, a measurement apparatus is mounted to said mounting hole, wherein said measurement apparatus is according to the first aspect of the present invention.

In an alternate second step, a measurement apparatus is mounted to said mounting hole, wherein the measurement apparatus is provided by the following steps: Providing a housing of said measurement apparatus with at least one first housing member having preferably, a low thermal conductivity. Providing a light source that emits light with a spectral distribution such that said light is absorbed at least partially and dependent on the concentration of said gaseous substance. Providing a light sensor that receives the light emitted by said light source. Forming a measurement region in said housing. Communicatively connecting said measurement region to said chamber for exchanging said gaseous content of the chamber. Arranging said light source within said housing and arranging said light sensor at least partially within said first housing member and outside said measurement region, wherein a light path from said light source to said light sensor is formed, such that light emitted by said light source passes through said measurement region before being received by said light sensor. Configuring at least a portion of the first housing member to provide a thermal shielding region that faces or forms a part of said measurement region on its one side and faces said light sensor on its other side, wherein said first housing member is formed to permit the passage of light along said light path through the thermal shielding region, and wherein said first housing member is configured, and in particular formed to limit the amount of heat transported from said measurement region to said light sensor, in particular along said light path.

In a preferred variant of the method, the incubator is configured according to the second aspect of the invention. In another preferred variant, the incubator is disinfectable by a high-temperature disinfection mode. In an additional or alternative preferred variant, the incubator is configured to measure the carbon dioxide concentration in said incubator.

This method corresponds to the manufacture of the incubators as already described in detail above in connection with the second aspect of the present invention. In particular, this method may also be used in connection with the various embodiments and variants of the incubator according to the second aspect of the present invention as described above. Especially, the embodiments and variants as well as potential benefits as already described above in detail in connection with the first and/or second aspect of the present invention also apply correspondingly to the method of manufacture according to the present invention.

A fourth aspect of the present invention is directed to a method of operating an incubator. The method comprises a first step, wherein an incubator according to the second aspect of the present invention is provided, or alternatively an incubator, e.g. a standard incubator as typically used for cell culture, as well as a measurement apparatus according to the first aspect of the invention are provided and said measurement apparatus is communicatively connected to the interior of said incubator, in particular to a chamber containing a gaseous content, or alternatively an incubator is manufactured according to the third aspect of the present invention. The method further comprises a measurement step and/or a disinfection step. In the measurement step the concentration of a gaseous substance in said gaseous content of the incubator is measured by said measurement apparatus, wherein said measurement apparatus is sensitive to said gaseous substance. In the disinfection step said incubator is disinfected by heating the interior of said incubator, in particular said chamber, to a predetermined temperature, which is in particular sufficient to disinfect and preferably sterilize the interior of said incubator, over a predetermined and/or sufficient time span, wherein during disinfection said measurement apparatus is communicatively connected to the interior of said incubator, and in particular mounted to said mounting hole. During disinfection in the disinfection step, said light sensor is protected from the heat, in particular from excessive heat and thus temperature, potentially damaging said light sensor, by said thermal shielding region. In a preferred variant, the interior of the incubator is heated to at least 60° C., preferably at least 90° C., more preferred to at least 130° C., and more preferred to at least 180° C. and preferably less than 1000° C., more preferred less than 300° C., and more preferred less than 210° C. during the disinfection step. In a preferred variant, the interior of the incubator is heated over a time span of at least 10 minutes, preferably at least 30 minutes, more preferred at least 180 minutes and preferably less than 48 hours, more preferred less than 25 hours, more preferred less than 8 hours. In a preferred variant, an excessive temperature of the light sensor caused by heat, which reaches said first housing member and/or said light sensor, is avoided by at least partially dissipating this heat to the outside of the incubator, in particular by a cooling apparatus, which may be a part of said first housing member. Additionally or alternatively, said first housing member and/or said light sensor may be connected to a heat reservoir with a temperature below the maximally tolerable temperature of the light sensor so as to dissipate heat there.

This method corresponds to the operation of the variants of incubators as already described in detail above in connection with the second and third aspect of the present invention. In particular, this method may also be used in connection with the various embodiments and variants according to the second or third aspect of the invention as described above. Preferably, respective method steps corresponding to the functionalities of the incubator as described in detail herein may be added. Especially, the embodiments and variants as well as potential benefits as already described above in detail in connection with the first, second, and/or third aspect of the invention also apply correspondingly to the method of operation according to the present invention. In particular, the temperature ranges and time spans are beneficial for a reliable disinfection and/or facilitating the operation of the incubator.

Further advantages, features and applications of the present invention are provided in the following detailed description of the exemplary embodiments and the appended figures. The same components of the exemplary embodiments are substantially characterized by the same reference signs, except if referred to otherwise or if other reference signs emerge from the context. In detail:

FIG. 1 schematically illustrates an exemplary embodiment of the measurement apparatus according to the invention, wherein a half of the first and second housing members, respectively, is shown cut out along the A axis for illustration purpose.

Figure 2:
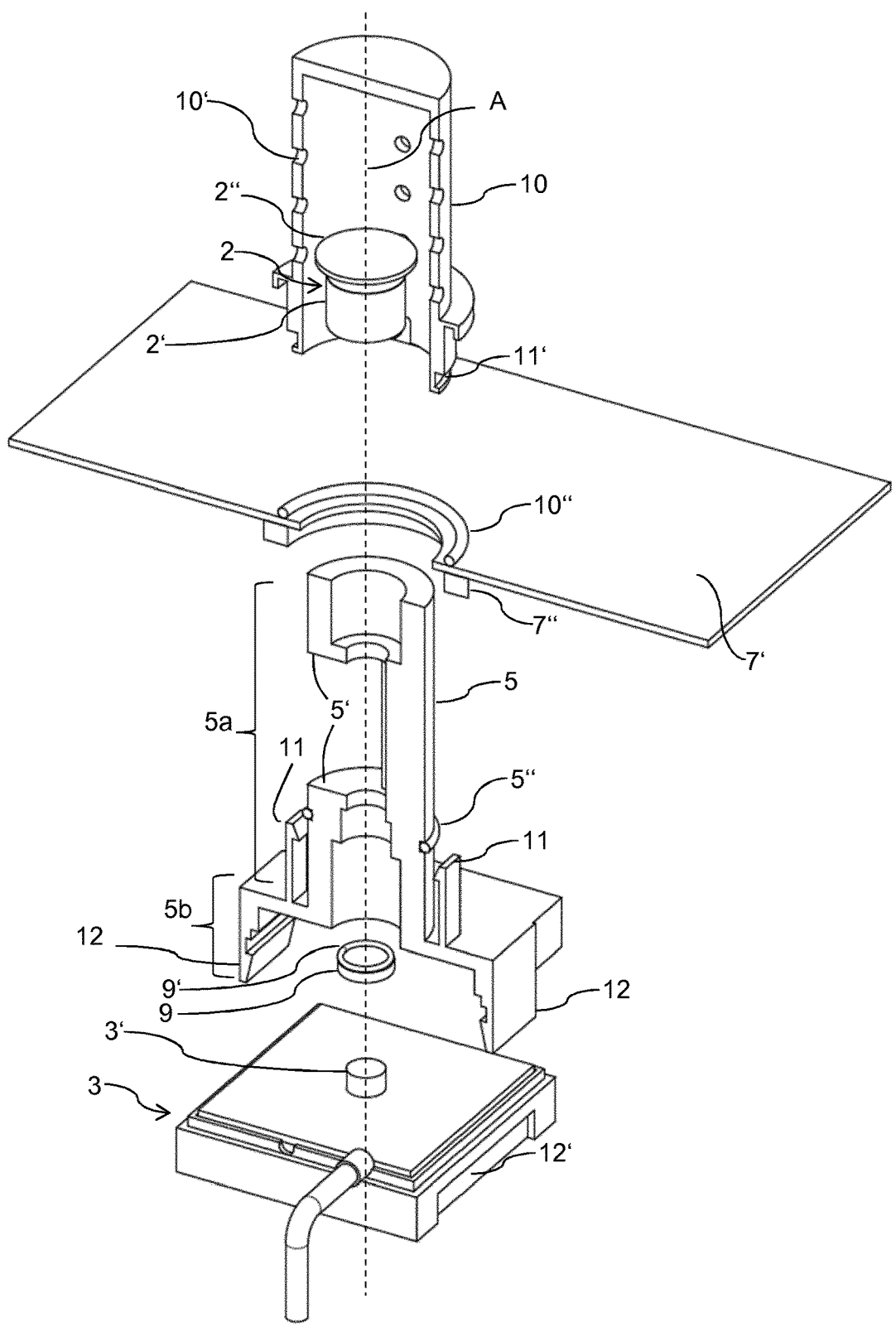

FIG. 2 shows an exploded view of the exemplary embodiment, wherein a half of the first and second housing members, respectively, is shown cut out along the A axis for illustration purpose.

FIG. 1 illustrates a measurement apparatus 1 according to a preferred embodiment of the present invention that is mounted to a wall 7' of an incubator. Preferably, the measurement apparatus 1 may be mounted to a rear wall 7' of a chamber 7 of the incubator. As described above, said chamber 7 may contain a gaseous content with a certain concentration of a gaseous substance. In particular, the measurement apparatus 1 depicted in FIG. 1 is adapted to measure the concentration of carbon dioxide. It is to be understood that said gaseous content may also contain none of said gaseous substance, i.e. the concentration of said gaseous substance is zero.

The measurement apparatus 1 is shown in a perspective sectional drawing. It comprises a light source 2, a light sensor 3, a housing 4 with a first housing member 5 and a second housing member 10, and a gas tight window 9. Preferably, the first housing member 5 is made of plastics, e.g. by injection molding, and/or the second housing member 10 is made of aluminum, e.g. by injection molding or aluminum casting. The light source 2 is mounted on one end of the first housing member 5, and the light sensor 3 is mounted on the other end of the first housing member 5. The light source 2 and the light sensor 3 face each other and a straight (not bent or bowed) light path is formed between them along the longitudinal direction represented by axis A. A holder part 5a of the first housing member 5 holding the light source 2 is inserted into the second housing member 10 and, thus, may be inside said chamber 7, when the measurement apparatus 1 is mounted to the incubator. A base part 5b of the first housing member 5 holding the light sensor 3 is not inside the second housing member 10 and, thus, may be outside said chamber 7 and/or incubator, when the measurement apparatus 1 is mounted to the incubator. In particular, this is beneficial to reduce the amount of heat transferred to the light sensor 3.

Within said first housing member 5 and said second housing member 10, a measurement region 6 is formed. This measurement region 6 can be communicatively connected to the chamber 7, wherein, particularly for this purpose, said first housing member 5 is provided with an opening or hole 5', and said second housing member 10 is provided with several holes 10' such that the gaseous content of the chamber 7 can flow from the chamber 7 into the measurement region 6 and vice versa. Alternatively, the first and/or the second housing member may be permeable for the gaseous content of the chamber 7. A further benefit of the holes 5', 10' as depicted in FIG. 1 is, that light may only enter in a direction that differs from the direction of the light path. Thus, light entering the measurement region 6 does not, at least directly, propagate to the light sensor 3. Preferably, the holes 10' of said second housing member 10 are bores through the wall of the second housing member having a cylindrical shape and a diameter between 1 mm and 10 mm, preferably a diameter of, at least essentially, 3 mm. The hole 5' corresponds to a relatively large cutout of the cylindrically shaped wall of the first housing member. It should be noted that a half of the first and second housings, respectively, in FIGS. 1 and 2 is shown cut out along the A axis for illustration purpose. The parts of the first and second housing members, which are not shown, have the same, in particular a symmetric, configuration as the parts of the first and second housing members, which are shown.

Said measurement region 6 has an at least essentially cylindrical shape and is defined by the first and second housing member 5, 10 at its circumference, by the light source 2 on its one end, and by the gas tight window 9 on its other end. Furthermore, the first housing member 5, the gas tight window 9, and the light sensor 3 define a thermal shielding region 8 that is separated from said measurement region 6 by the gas tight window 9 and the first housing member 5. In this manner, the gaseous content of the measurement region 6 and/or the chamber 7 cannot pass into the side of said thermal shielding region 8' facing the light sensor 3, and the transfer of heat by the gaseous content to said light sensor 3 is prevented.

FIG. 2 shows an exploded view of the exemplary embodiment. For greater clarity, not all parts of features are denoted with a reference sign. As in FIG. 1, said light source 2, said light sensor 3, said first housing member 5 as well as said second housing member 10, said rear wall 7' of the incubator, and said gas tight window 9 are illustrated. Preferably, said gas tight window 9 is made of sapphire glass and/or has a diameter of 10 mm. Preferably, said second housing member 10 has a cylindrical shape with an outer diameter of 30 mm and/or a length of 30 mm to 50 mm.

Furthermore, a gasket of the said first housing member 5", a gasket of said second housing member 10", and a gasket of said gas tight window 9' are illustrated in FIG. 2. The gasket of the said first housing member 5" improves the seal between said first housing member 5 and said second housing member 10. Thus, in particular, this gasket 5" reduces the amount of said gaseous content of said chamber 7 that may flow to the outside and/or to the light sensor 3 through the connection area of said first and second housing member 5, 10. The gasket of said gas tight window 9' improves the seal between said first housing member 5 and said gas tight window 9. Thus, in particular, this gasket 9' reduces the amount of said gaseous content that may flow from the measurement region 6 to the side 8' of the thermal shielding 8' region facing the light sensor 3. The gasket of said second housing member 10" improves the seal between said second housing member 10 and said rear wall 7'. Thus, in particular, this gasket 10" reduces the amount of said gaseous content that may flow from the chamber 7 to the outside. Preferably, as depicted in FIG. 2, said second housing member 10 has a groove for receiving, at least partially, said gasket of the second housing member 10", whereby the seal is improved. Moreover, said second housing member 10 preferably comprises a screw thread, not depicted, such that it can be fastened against the rear wall 7' by means of a screw nut 7". Additionally, by fastening said second housing member 10 against said rear wall 7' said gasket 10" is pressed against the rear wall 7' and into the groove for receiving said gasket 10", thereby further improving the seal.

As depicted in FIG. 2, said first housing member 10 preferably comprises one or more first hooks 11 as well as one or more second hooks 12. Said first hooks 11 are configured to engage with a corresponding groove 11' of the second housing member 10. This may be beneficial to connect said first housing member 5 and said second housing member 10 with each other and/or to facilitate manufacture, installation and/or maintenance of the measurement apparatus 1. Said second hooks 12 are configured to engage with a corresponding groove 12' of the light sensor 3. Thereby, in particular, the light sensor 3 can be mounted to the first housing member 5 independently of the mounting and/or installation of said first housing member 5 onto/into said second housing member 10 as well as of said measurement apparatus 1 to the incubator. Preferably, the light sensor 3 is preinstalled on the first housing member 5.

The light source 2 preferably comprises a heatable body 2' and a heating device 2". Preferably, the heating device 2" converts electrical energy into heat and heats said heatable body 2', in particular a brass rod. Consequently, the brass rod 2' will emit light with a spectrum dependent on its temperature and typically broad enough to provide light of a wavelength for measurement as well as light of a wavelength for reference.

A particularly preferred light source is the Infrared Radiation Source JSIR350-4-AL-R-D6.0-0-0 of Micro-Hybrid Electronic GmbH, see e.g. http://www.micro-hybrid.de/fileadmin/user/IR-systems-documents/Datenblaetter/Strahler/JSIR350-4-AL-R-D6.0-0-0.pdf The light sensor 3 preferably comprises one or more thermopiles 3' for converting the energy of the incident light into an electrical signal and one or more filter elements for filtering out or permitting the passage of light with a certain wavelength, e.g. to provide a reference and a measurement signal. In particular, for measuring the carbon dioxide concentration, said light sensor 3 comprises two thermopiles and two corresponding filter elements, wherein the filter element only permits the passage of light with a wavelength of 4.26 µm to one of the thermopiles for providing a measurement signal, and wherein the other filter element only permits the passage of light with a wavelength of 3.95 µm to the other of the thermopiles for providing a reference signal. In particular, the 4.26 µm filter has a bandwidth of 180 nm and/or the 3.95 µm filter has a bandwidth of 90 nm in order to ensure that only light with relevant wavelengths is passed to the respective thermopiles. A particularly preferred light sensor or part of the light sensor comprising two thermopiles and filters is the HIS E222, particularly the model HIS E222 F3.91/90 F4.26/180 G4300, of HEIMANN Sensor GmbH, see e.g. http://www.heimannsensor.com/Datasheet%20HIS%20E222%20F1%20F2%20Gx.pdf While above at least one exemplary embodiment of the present invention has been described, it has to be noted that a great number of variation thereto exists. Furthermore, it is appreciated that the described exemplary embodiments only illustrate non-limiting examples of how the present invention can be implemented and that it is not intended to limit the scope, the application or the configuration of the herein-described apparatus' and methods. Rather, the preceding description will provide the person skilled in the art with constructions for implementing at least one exemplary embodiment of the invention, wherein it has to be understood that various changes of functionality and the arrangement of the elements of the exemplary embodiment can be made, without delegating from the subject-matter defined by the appended claims and their legal equivalents.

LIST OF REFERENCE SIGNS 1 measurement apparatus
2 light source
2' heatable body, in particular a brass rod
2" heating device
3 light sensor
3' thermopile of light sensor
4 housing
5 first housing member
5a holder part
5b base part
5' hole in first housing member
5" gasket of first housing member
6 measurement region
7 chamber of incubator
7' wall of incubator, in particular rear wall of chamber
7" screw nut
8 thermal shielding region 8' side of said thermal shielding region facing light sensor
9 gas tight window
9' gasket of gas tight window
10 second housing member
10' hole in second housing member
10" gasket of second housing member
11 first hook of first housing member
11' groove corresponding to first hook
12 second hook of first housing member
12' groove corresponding to second hook

The invention claimed is:

1. A measurement apparatus (1) for measuring the concentration of a light absorbing gaseous substance in a chamber (7), in particular a carbon dioxide measurement apparatus, comprising:
a light source (2);
a light sensor (3); and
a housing (4) comprising at least one first housing member (5);
wherein:
from said light source (2) to said light sensor (3) a light path is formed that passes through a measurement region (6) within the housing (4) communicatively connectable to the chamber (7) for exchanging a gaseous content of the chamber (7);
the light source (2) is configured to emit light with a spectral distribution such that said light is absorbed at least partially and dependent on the concentration of said gaseous substance in said gaseous content while passing through said measurement region (6);
said light sensor (3) is at least partially arranged within said first housing member (5) and outside said measurement region (6) and is configured to receive the light emitted by the light source (2) after it has passed through the measurement region (6);
said first housing member (5) comprises a thermal shielding region (8) facing or forming a part of said measurement region (6) on its one side and facing said light sensor (3) on its other side (8'); and
said thermal shielding region (8) is configured to permit the passage of light along said light path from its one side to its other side (8')
characterized in that:
the housing (4) comprising at least one second housing member (10);
the at least one first housing member (5) is at least partially arranged within said second housing member (10); and
a gasket (10") is arranged around said second housing member (10) such that it seals a connection area between the measurement apparatus (1) and said chamber (7), when the measurement apparatus is mounted to said chamber, the first housing member having a base part (5b) for connecting the light sensor and a holder part (5a) for holding the light source, the holder part (5a) being inserted into said second housing member (10) for mounting the housing (4) to the chamber by means of said second housing member (10) and the holder part (5a) being capable to be positioned inside said chamber (7) while said base part (5b) is positioned outside the chamber (7).

2. A measurement apparatus (1) according to claim 1, wherein said thermal shielding region (8) has a tubular inner shape.

3. A measurement apparatus (1) according to claim 2, wherein:

the inner shape of said thermal shielding region (8) is elongated and long enough in relation to its width to provide a desired thermal shielding of said light sensor (3).

4. A measurement apparatus (1) according to claim 1, wherein:
an at least essentially gas tight window (9) is arranged within said thermal shielding region (8) and within said light path;
said window (9) separates said measurement region (6) from said light sensor (3); and
said window (9) is configured:
to permit the passage of light, in particular light with a wavelength absorbed by the gaseous substance, to said light sensor (3); and
to prevent the passage of gas from said chamber (7) or said measurement region (6) to said light sensor (3) in cooperation with the side (8') of said thermal shielding region (8) facing said light sensor (3).

5. A measurement apparatus (1) according to claim 1, wherein:
said light source (2) is configured to emit light with at least two different wavelengths;
the light of one of the at least two wavelengths being absorbed by the gaseous substance while the light of the other of the at least two wavelengths being not absorbed; and
said light sensor (3) is configured to receive the at least two different wavelengths and to provide a signal characterizing the light intensity for each of the at least two different wavelengths, i.e. a measurement signal and a reference signal.

6. A measurement apparatus (1) according to claim 1, wherein a reference light path is formed from said light source (2) to said light sensor (3) that does not pass through said measurement region (6).

7. A measurement apparatus (1) according to claim 1, wherein said light sensor (3) comprises:
at least one first optical filter element that permits the passage of light with a wavelength that is absorbed by the gaseous substance and
at least one second optical filter element that filters out light with a wavelength that is absorbed by the gaseous substance.

8. A measurement apparatus (1) according to claim 1, wherein said light sensor (3) comprises a thermopile (3') to convert the received and in particular filtered light into electrical energy serving as a signal characterizing the light intensity, in particular the light intensity of the light not being filtered out.

9. A measurement apparatus (1) according to claim 1, wherein the light source (2) comprises a heatable body (2') to radiate said light, wherein said light is infrared light.

10. A measurement apparatus (1) according to claim 1, wherein said first housing member (5) is made of a material with low thermal conductivity.

11. A measurement apparatus (1) according to claim 1, wherein:
said housing (4) comprises at least a second housing member (10), in particular made of metal;
the at least one first housing member (5) and the at least one second housing member (10) are each provided with one or more holes (5', 10') to permit the passage of said gaseous content from said chamber (7) to said measurement region (6) and vice versa; and
said housing (4), in particular the at least one first and/or second housing member (5, 10), is configured to limit, and in particular to prevent the entry of light into said measurement region (6), in particular in a direction along said light path or said reference light path.

12. An incubator, in particular for cell culture, comprising:
    a chamber (7); and
    at least one measurement apparatus (1) for measuring the concentration of a light absorbing gaseous substance according to one of the preceding claims;
    wherein:
    said chamber (7) is configured to contain a gaseous content which may contain said gaseous substance, in particular to provide a controlled environment particularly for cell culture; and
    said measurement region (6) of the at least one measurement apparatus (1) being communicatively connected to said chamber (7) of the incubator to permit the exchange of said gaseous content.

13. An incubator according to claim 12, further comprising:
    a front door;
    a rear wall (7') opposite to the front door; and
    one or more gas inlets, wherein one of the gas inlets is configured to supply said gaseous substance into said chamber (7);
    wherein
    said rear wall (7') comprises a mounting hole;
    said at least one measurement apparatus (1) extends through said mounting hole in the rear wall (7'); and
    said mounting hole and said gas inlets are positioned such that the minimum distance between said mounting hole and said gas inlets is at least one fourth of the diagonal length of said rear wall.

14. A method of manufacture of an incubator that is disinfectable by heating, particularly by a high-temperature disinfection mode, and configured to measure the concentration of a light absorbing gaseous substance in a gaseous content of said incubator, in particular for measuring the carbon dioxide concentration in said incubator, comprising the steps:
    providing an incubator with at least one mounting hole, wherein the incubator comprises a chamber (7) to contain said gaseous content;
    mounting a measurement apparatus (1) at said mounting hole, wherein said measurement apparatus (1) is configured according to claim 1 and/or provided by the steps:
    providing a housing (4) of said measurement apparatus (1) with at least one first housing member (5) and at least one second housing member (10);
    providing a light source (2) that emits light with a spectral distribution such that said light is absorbed at least partially and dependent on the concentration of said gaseous substance;
    providing a light sensor (3) that receives the light emitted by said light source (2);
    forming a measurement region (6) in said housing (4);
    communicatively connecting said measurement region (6) to said chamber (7) for exchanging said gaseous content of the chamber (7);
    arranging said light source (2) within said housing (4) and arranging said light sensor (3) at least partially within said first housing member (5) and outside said measurement region (6) so as to form a light path from said light source (2) to said light sensor (3), wherein light emitted by said light source (2) passes through said measurement region (6) before being received by said light sensor (3);
    configuring at least a portion of the first housing member (5) to provide a thermal shielding region (8) that faces or forms a part of said measurement region (6) on its one side and faces said light sensor (3) on its other side, wherein said first housing member (5) is formed to permit the passage of light along said light path through the thermal shielding region (8) and is configured, and in particular formed to limit the amount of heat transported from said measurement region (6) to said light sensor (3), in particular along said light path;
    arranging the at least one first housing member (5) at least partially within said second housing member (10) for mounting the housing (4) to the chamber by means of said second housing member (10) in a mounted position, the first housing member having a base part (5b) for connecting the light sensor and a holder part (5a) for holding the light source and wherein the holder part (5a) is positioned inside said chamber (7) while the base part (5b) is positioned outside the chamber (7);
    providing a gasket (10") arranged around said second housing member (10) such that it seals a connection area between the measurement apparatus (1) and said chamber (7), when the measurement apparatus is mounted to said chamber.

15. A method of operating an incubator, comprising:
    providing an incubator according to claim 12, or providing an incubator with a measurement apparatus (1) according to claim 1 and communicatively connecting said measurement apparatus (1) to the interior of said incubator, in particular to a chamber (7) containing a gaseous content, or manufacturing an incubator according to claim 14;
    the method further comprising one or more of the following steps:
    measuring the concentration of a gaseous substance in said gaseous content of the incubator by said measurement apparatus (1), wherein said measurement apparatus (1) is sensitive to said to gaseous substance;
    disinfecting said incubator by heating the interior of said incubator, in particular said chamber (7), to a predetermined temperature, which is in particular sufficient to disinfect and preferably sterilize the interior of said incubator, over a predetermined and/or sufficient time span, wherein said measurement apparatus (1) is communicatively connected to the interior of said incubator, and in particular mounted into said mounting hole during disinfection and wherein said light sensor (3) is protected from the heat, particularly from excessive heat and thus temperature potentially damaging said light sensor (3), by said thermal shielding region (8).

* * * * *